US009345519B1

(12) United States Patent
Poirier et al.

(10) Patent No.: US 9,345,519 B1
(45) Date of Patent: May 24, 2016

(54) PEDICLE SCREW

(75) Inventors: David Poirier, Danville, CA (US);
Robert Rovner, Danville, CA (US)

(73) Assignee: Presidio Surgical, Inc., Alamo, CA (US)

( * ) Notice: Subject to any disclaimer, the term of this patent is extended or adjusted under 35 U.S.C. 154(b) by 932 days.

(21) Appl. No.: 13/135,359

(22) Filed: Jul. 1, 2011

Related U.S. Application Data

(60) Provisional application No. 61/398,929, filed on Jul. 2, 2010.

(51) Int. Cl.
*A61B 17/70* (2006.01)

(52) U.S. Cl.
CPC .................................. *A61B 17/7032* (2013.01)

(58) Field of Classification Search
CPC .................................................. A61B 17/7032
USPC .................................................. 606/264–279
See application file for complete search history.

(56) References Cited

U.S. PATENT DOCUMENTS

| 5,102,412 | A  | * | 4/1992  | Rogozinski ................. 606/86 A |
| 6,280,443 | B1 | * | 8/2001  | Gu et al. ....................... 606/264 |
| 8,167,912 | B2 | * | 5/2012  | Jacofsky et al. ............. 606/267 |
| 8,241,329 | B2 | * | 8/2012  | Abdou .......................... 606/247 |
| 2006/0129149 | A1 | * | 6/2006  | Iott et al. ........................ 606/61 |
| 2007/0233089 | A1 | * | 10/2007 | DiPoto et al. .................. 606/61 |
| 2007/0270813 | A1 | * | 11/2007 | Garamszegi .................... 606/61 |
| 2008/0086132 | A1 | * | 4/2008  | Biedermann et al. .......... 606/61 |
| 2009/0093843 | A1 | * | 4/2009  | Lemoine et al. ............. 606/246 |
| 2009/0099605 | A1 | * | 4/2009  | Fallin et al. .................. 606/252 |
| 2009/0204155 | A1 | * | 8/2009  | Aschmann .................... 606/264 |
| 2009/0248078 | A1 | * | 10/2009 | Dant ............................. 606/246 |
| 2010/0049255 | A1 | * | 2/2010  | Matthis et al. ............... 606/279 |
| 2010/0234891 | A1 | * | 9/2010  | Freeman et al. ............. 606/266 |
| 2010/0241170 | A1 | * | 9/2010  | Cammisa et al. ............. 606/264 |
| 2010/0286731 | A1 | * | 11/2010 | Biedermann et al. ........ 606/264 |
| 2010/0331887 | A1 | * | 12/2010 | Jackson et al. .............. 606/264 |
| 2011/0087293 | A1 | * | 4/2011  | Ferreira et al. .............. 606/265 |
| 2011/0137350 | A1 | * | 6/2011  | Stad et al. .................... 606/264 |
| 2012/0041490 | A1 | * | 2/2012  | Jacob et al. .................. 606/264 |
| 2012/0221058 | A1 | * | 8/2012  | Stad et al. .................... 606/264 |
| 2012/0226317 | A1 | * | 9/2012  | Potash .......................... 606/264 |
| 2012/0303064 | A1 | * | 11/2012 | Walker et al. ................ 606/270 |
| 2012/0310284 | A1 | * | 12/2012 | Gerchow ...................... 606/264 |
| 2012/0330364 | A1 | * | 12/2012 | Jacofsky et al. ............. 606/278 |
| 2013/0066376 | A1 | * | 3/2013  | Biedermann et al. ........ 606/278 |
| 2013/0096618 | A1 | * | 4/2013  | Chandanson et al. ....... 606/278 |
| 2013/0096621 | A1 | * | 4/2013  | Biedermann et al. ........ 606/279 |
| 2013/0110172 | A1 | * | 5/2013  | Biedermann et al. ........ 606/278 |
| 2013/0165977 | A1 | * | 6/2013  | Biedermann et al. ........ 606/278 |
| 2013/0172935 | A1 | * | 7/2013  | Matthis et al. ............... 606/278 |

(Continued)

*Primary Examiner* — Ellen C Hammond
*Assistant Examiner* — Stuart S Bray
(74) *Attorney, Agent, or Firm* — Heisler & Associates

(57) ABSTRACT

The pedicle screw assembly includes a threaded screw extending from a tip to a head. A tulip head is coupled to the head of the screw. A hollow interior of the tulip head has a slot which receives a spine rod therein. A locking nut and preferably also a saddle and locking cap bear on the spine rod and secure the spine rod within the slot of the tulip head and against the head of the screw. The head of the screw is semi-spherical. Portions of the tulip head and structures residing within the tulip head which abut against the head are also preferably semi-spherical. The saddle and locking cap abut against the spine rod with semi-cylindrical surfaces, such that surface contact is provided against the spine rod for secure coupling of the spine rod to the pedicle screw.

7 Claims, 4 Drawing Sheets

(56) References Cited

U.S. PATENT DOCUMENTS

| | | | |
|---|---|---|---|
| 2013/0197586 A1* | 8/2013 | Matthis et al. | 606/278 |
| 2013/0274805 A1* | 10/2013 | Jackson | 606/264 |
| 2013/0331892 A1* | 12/2013 | Peterson et al. | 606/279 |
| 2013/0345756 A1* | 12/2013 | Berrevoets et al. | 606/278 |
| 2013/0345758 A1* | 12/2013 | Biedermann et al. | 606/279 |
| 2014/0005726 A1* | 1/2014 | Jackson | 606/273 |
| 2014/0012319 A1* | 1/2014 | Jackson | 606/266 |

* cited by examiner

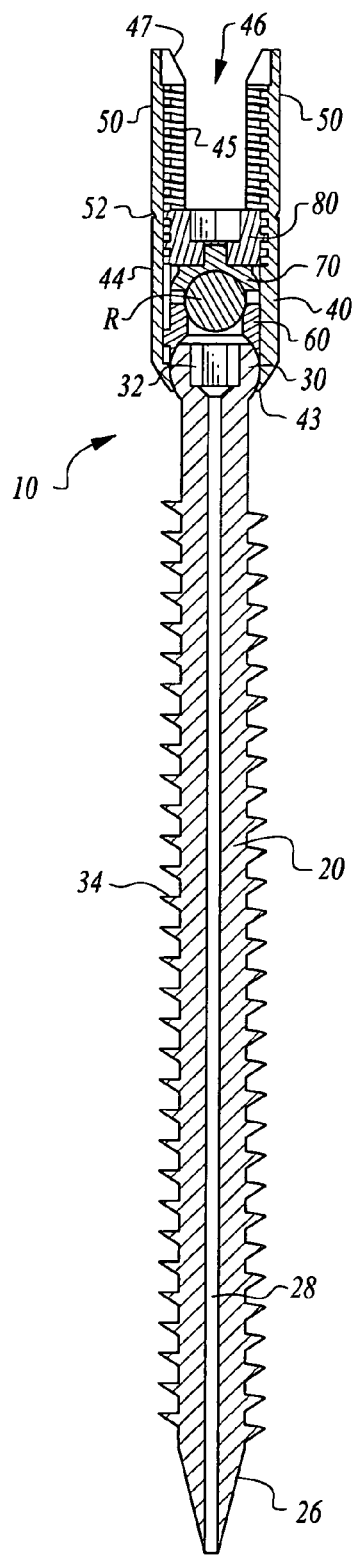
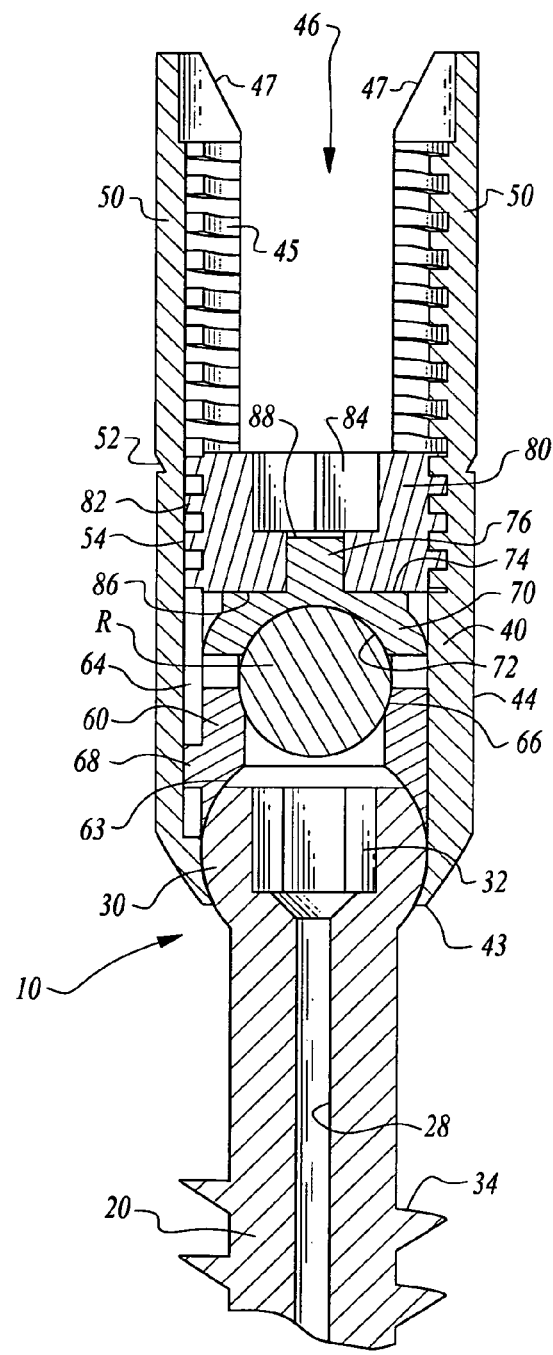
Fig. 5
Fig. 6

PEDICLE SCREW

CROSS-REFERENCE TO RELATED APPLICATIONS

This application claims benefit under Title 35, United States Code §119(e) of U.S. Provisional Application No. 61/398,929 filed on Jul. 2, 2010.

FIELD OF THE INVENTION

The following invention relates to screws for attaching to the pedicle of a vertebra and for securing a spine rod to the vertebra through the pedicle screw. More particularly, this invention relates to pedicle screws which include a configuration at a head thereof for secure attachment of the pedicle screw to a spine rod.

BACKGROUND OF THE INVENTION

When performing spinal fusion procedures and when otherwise required to immobilize portions of the spine, one method for such spine immobilization is to use a spine rod running generally parallel with the spine and anchoring the rod to the spine through pedicle screws. Pedicle screws are bone screws which are configured to thread into the pedicle of a vertebrae. A head of the pedicle screw is specially configured so that it can clamp onto the rod. The pedicle screw thus acts as an interface to couple the rod to the spine. Through utilization of multiple pedicle screws, a single rigid rod can extend along the spine and transfer some of the loads which might otherwise cause the spine to be mobile.

Pedicle screws are known in the prior art to provide this required function. As spinal fusion procedures and other related procedures can be quite complex and difficult, it is beneficial to make the pedicle screw as easy to use as possible and to work reliably and consistently. Such enhancements provide a direct benefit in simplifying an otherwise very complex procedure, ultimately improving outcomes for the patient.

SUMMARY OF THE INVENTION

The pedicle screw of this invention includes an elongate screw with threads on an outer surface thereof. This screw is preferably cannulated, such as to facilitate use in MIS cases. In one example, the cannulated screw is configured for use with a 0.062 guide wire. As an option, the screw could be also provided without being cannulated.

The threads are preferably relatively aggressive pitch so that fewer turns are required for implantation of the screw into the pedicle. Cutting flutes are preferably provided near a tip of the screw for self-tapping and to assist in starting the screw in the threading procedure into the pedicle.

A head portion of the screw is preferably low profile and having a generally spherical contour. A face of this head is preferably recessed to receive some form of torque applying tool. In one form, this recess is hexagonal in form to receive an Allen wrench type driver tool. Other recess configurations can be provided for use with other tool configurations for applying torque to the screw for advancement or removal of the screw. By making the head semi-spherical, ease in coupling to the rod at various different angles is facilitated as described further herein below.

To engage the rod to the screw, a tulip head is provided. The tulip head is generally cylindrical in form with a slot extending down along the central axis so that the tulip head has a U-shaped form when viewed from a side thereof. An interior of this tulip head is preferably substantially hollow with threads on an inner surface thereof. A lower end of the tulip head has a hole passing therethrough which is sized just large enough to allow the screw and threads to pass therethrough, but which prevents the head from passing therethrough. Thus, the tulip head can be advanced from a tip of the screw up towards the head of the screw with the tulip head stopping adjacent the head of the screw.

The tulip head can pivot relative to the screw somewhat. The slot in the tulip head has a width similar to a diameter of the rod to which the pedicle screw is to be attached. The tulip head preferably has tabs which extend a length of the tulip head axially. These tabs are configured with a fracture line which allows the tabs to be removed if the tabs are not required. An outer surface of the tulip head is preferably faceted somewhat so that the tulip head can be readily rotated as required to align the slot in the tulip head with the orientation desired for the rod.

Above the head of the screw and within the tulip head, but below the position for the rod, a saddle is preferably provided. This saddle is generally cylindrical in form with a semi-cylindrical slot in an upper surface thereof. The saddle is sized to fit snugly within an interior of the tulip head directly adjacent the head of the screw and near a lower end of the tulip head. The saddle preferably floats within the tulip head, but could alternatively be keyed so that the semi-cylindrical slot in the saddle remains aligned with the slot in the tulip head at all times.

A locking cap and locking nut assembly are provided within the interior of the tulip head and above the position for the rod. The locking cap has a semi-cylindrical recess in a lower surface thereof configured to be directly adjacent the rod and on a side of the rod opposite the saddle. An upper surface of the locking cap opposite this semi-cylindrical slot preferably includes a pin extending upward therefrom. A locking nut is provided with threads complemental to threads within the interior of the tulip head. This locking nut can be advanced downward within the tulip head to press the locking cap against the rod.

The locking nut preferably has a hole therein which can receive the pin in the top of the locking cap. In one embodiment the hole in the locking nut is sized to fit snugly with the post on the top of the locking cap so that the post on the locking cap and the hole in the locking nut keep the locking cap aligned with the locking nut, while still allowing relative rotation between the locking nut and the locking cap. As an alternative, some amount of play can be provided within this hole in the bottom of the locking nut so that some degree of play is facilitated between the locking nut and the locking cap.

When the locking nut is tightened against the locking cap and the locking cap is pressed against the rod, the rod is pressed down into the saddle and held tightly within the tulip head and adjacent the screw. In this way, the screw and rod have been secured together by the entire pedicle screw assembly.

Two different locking cap/nut assemblies are shown herein which slightly vary from each other. With the locking cap of the second embodiment a key is provided on a side of the locking cap which keeps the locking cap from rotating relative to the tulip head. The tulip head would include a slot therein which would keep this key of the locking cap aligned therein, so that the semi-cylindrical recess on the lower surface of the locking cap would always remain aligned with the slot in the tulip head. Note that because the face of the head of the screw is flat and the lower surface of the saddle is flat, once the locking nut is tightened within the tulip head, pressure against the saddle flat surface which is bearing against the flat surface of the head of the screw keeps the tulip head from being able to pivot relative to the screw. An upper end of the locking nut includes a recess therein for receipt of a torque applying tool, such as a hexagonal recess configured to receive an Allen wrench therein. Various other recesses could alternatively be utilized for fitting with other torque applying tools.

The threads on the locking nut are preferably squared off as well as the threads within the interior of the tulip head. Such threads provided resistance to cross-threading and provide an easy start for initiating the threading process for the locking nut. The saddle and locking cap are preferably configured with their semi-cylindrical recesses facing the rod and configured to maximize physical contact between the saddle and locking cap and the rod. In this way, maximum gripping force on the rod can be facilitated while minimizing stress concentrations.

The entire pedicle screw assembly is configured to simplify screwdriver engagement with a screw designed for coaxial alignment and ease of screwdriver purchase. The tulip head is configured to be polyaxial. The rod can be precurved/prebent for lordosis. A low profile polyaxial head is provided to accommodate varying anatomical and clinical situations. The self-taping tapered bone screw and buttress thread are designed for maximum strength, screw purchase and pullout resistance. In particular embodiments shown herein it is preferably configured for both lordosed and straight 5.5 millimeter rods in lengths up to 400 millimeters, but could vary with appropriate modification to the design shown herein.

The overall assembly of the pedicle screw is low profile to most readily facilitate working with the pedicle screw assembly and minimizing impact on adjacent body structures. With the tabs at the top of the tulip head, the rod insertion process is simplified and eliminates the need for rod reduction instrumentation. Screws of 30-85 millimeters can be accommodated with screw diameters from 4.0-8.5 millimeters. Rods can be accommodated between 30 and 120 millimeters for pre-lordosed lengths and between 30 and 400 millimeters for straight rods.

Overall the pedicle screw system is intended to provide immobilization and stabilization of spinal segments in skeletally mature patients as an adjunct to fusion in the treatment of the following acute and chronic instabilities or deformities of thoracic, lumbar and sacral spine: degenerative disc disease (DDD) (defined of back pain of discogenic origin with degradation of the disc confirmed by history and radiographic studies); spondylolisthesis; trauma (i.e. fracture or dislocation); spinal stenosis; tumor; pseudoarthosis; and failed previous fusion.

OBJECTS OF THE INVENTION

Accordingly, a primary object of the present invention is to provide a pedicle screw which is easy to secure to a pedicle of a vertebra and easy to securely attach to a spine rod.

Another object of the present invention is to provide a pedicle screw which provides a secure connection to a spine rod and to a vertebra.

Another object of the present invention is to provide a pedicle screw for use in a spinal fusion procedure or other spine utilization procedure.

Another object of the present invention is to provide a pedicle screw which is adjustable to accommodate various different orientations of the pedicle screw and spine rod relative to each other.

Another object of the present invention is to provide a pedicle screw and spine rod combination for immobilizing a spine, such as during spinal fusion of adjacent vertebrae.

Another object of the present invention is to provide a pedicle screw with a low profile contour which accommodates varying anatomical and clinical situations.

Another object of the present invention is to provide a pedicle screw which has spine rod engaging nut portions which are unlikely to be cross-threaded.

Another object of the present invention is to provide a method for securing a spine rod to multiple vertebrae through use of pedicle screws.

Other further objects of the present invention will become apparent from a careful reading of the included drawing figures, the claims and detailed description of the invention.

BRIEF DESCRIPTION OF THE DRAWINGS

FIG. 5 is a full sectional view of the pedicle screw and spine rod assembly.

FIG. 6 is a full sectional view providing detail for a portion of that which is shown in FIG. 5.

DESCRIPTION OF THE PREFERRED EMBODIMENT

Figures 1, 2:
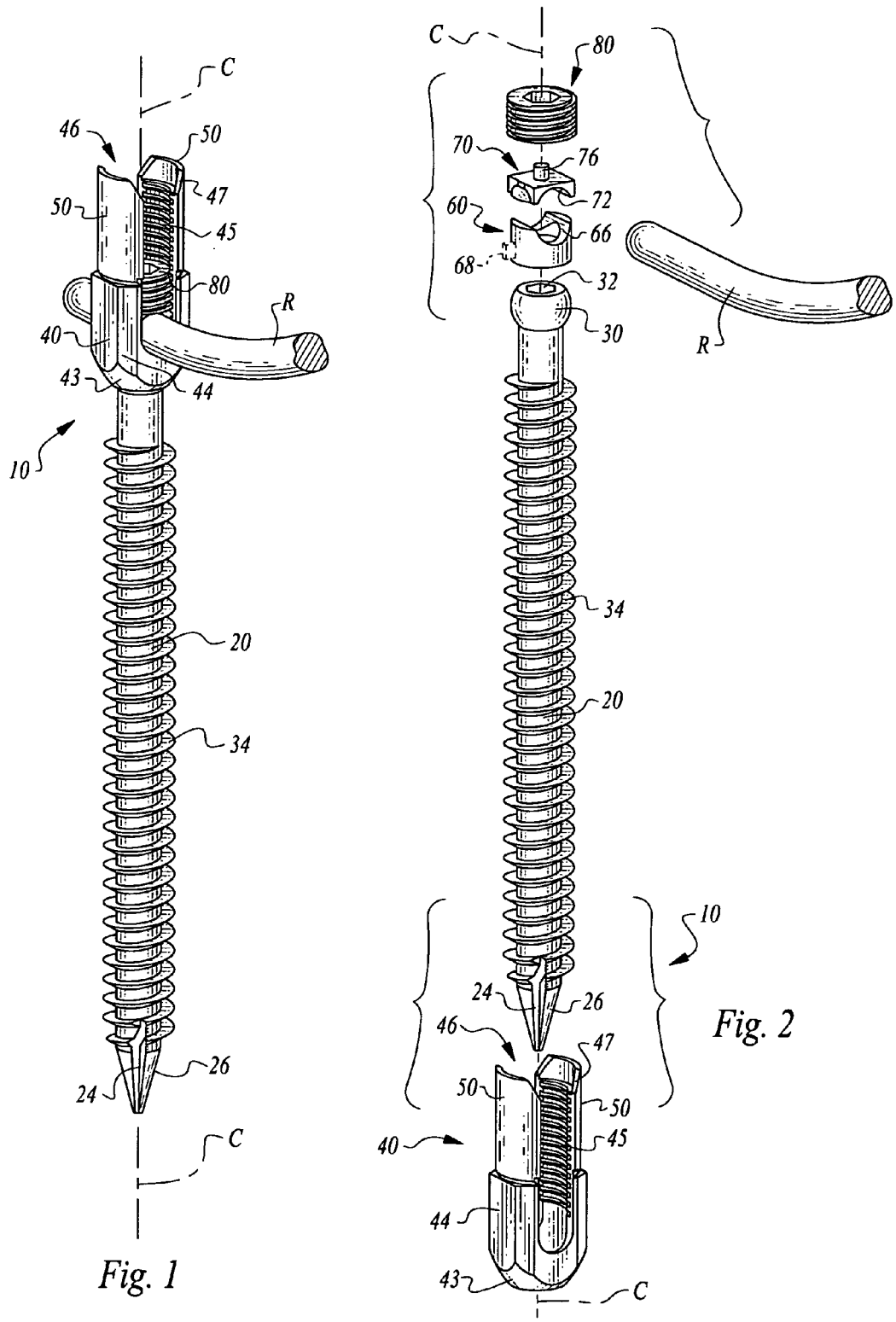
FIG. 1 is a perspective view of a pedicle screw and portion of a spine rod with the spine rod captured to the pedicle screw.
FIG. 2 is a perspective view similar to that which is shown in FIG. 1 but with separate structures exploded away from each other.

Referring to the drawings, wherein like reference numerals represent like parts throughout the various drawing figures, reference numeral 10 is directed to a pedicle screw assembly (FIGS. 1, 2 and 5). This assembly 10 includes a screw 20 element along with a tulip head 40 and a locking nut 80 which engages with the tulip head 40 to secure a spine rod R within the tulip head 40 and adjacent a head 30 of the screw 20. With this assembly 10 a spine rod can be secured to vertebrae of a spine to immobilize portions of the spine, such as during a spinal fusion procedure.

In essence, and with particular reference to FIGS. 1 and 2, basic details of the assembly 10 of this invention are described, according to a preferred embodiment. The assembly 10 includes the screw 20 element which has a head 30 on a portion of the screw 20 opposite a tip 26. A tulip head 40 is provided adjacent the head 30 of the screw 20. The tulip head 40 is configured with a hollow interior and with two ends sized so that the entire screw 20 can pass through one of the ends of the tulip head 40 and all of the screw 20 except for the head 30 can pass through the other of the ends of the tulip head 40, defining a collar 43. The tulip head 40 is thus coupled to the screw 20 adjacent the head 30. The tulip head 40 includes break off tabs 50 defining an upper portion of the tulip head 40 on either side of a slot 46 which extends down into the tulip head 40 along a plane coextensive with a centerline C of the tulip head 40. The break off tabs 50 can be optionally broken off and removed from the tulip head 40 if not required after installation of the screw 20 and securing of a spine rod R thereto.

The tulip head 40 includes inner threads 45 on an inside surface thereof which facilitate engagement with a locking nut 80 for securing of a spine rod R within the slot 46 of the tulip head 40 and against the head 30 of the screw 20. Preferably, a saddle 60 resides within this interior of the tulip head 40 to be positioned between the spine rod R and the head 30 of the screw 20. A locking cap 70 is preferably configured to reside between the spine rod R and the locking nut 80 in a most preferred form of this invention. When the locking nut 80 is rotated to tighten the lock nut 80 within the tulip head 40 and advance the locking nut 80 towards the head 30 of the screw 20, the locking cap 70 and saddle 60 are drawn into compression with the spine rod R to trap the spine rod R between the saddle 60 and the locking cap 70, so that the entire pedicle screw assembly 70 is rigidly secured to the spine rod R.

More specifically, and with particular reference to FIGS. 1, 2 and 5, particular details of the screw 20 element and associated screw head 30 are described, according to this most preferred embodiment. The screw 20 in this embodiment is preferably cannulated with a central bore 28 passing therethrough. A tip 26 of the screw 20 preferably includes a fluted tapping groove 24 so that the screw 20 can be at least partially self-tapping. Because the screw 20 is cannulated, it can be passed along a guide wire which has been initially placed precisely where desired. Typically, such assembly occurs with the assistance of a fluoroscope or other imaging device to ensure that the guide wire and the pedicle screw 20 are being precisely positioned where desired within the pedicle of the vertebra.

The screw head 30 defines an end of the screw 20 most distant from the tip 26. The screw head 30 preferably includes a driver recess 32 extending along a centerline C of the screw 20 into the head 30. The driver recess 32 is preferably formed in the center of a flat surface defining a portion of the screw head 30 most distant from the tip 26. Threads 34 extend along the screw 20 between the head 30 and the tip 26. Preferably, a short threadless shank is provided just below the head 32. The threads 34 preferably have an aggressive pitch so that fewer turns are required for insertion of the screw. Such aggressive pitch is also facilitated by provision of the cutting flutes adjacent the tip 26 for tapping of threads into the pedicle of the vertebra.

Screws of various different diameters and lengths can be provided. In one embodiment the screws range in length from 30.0 to 85.0 millimeters with a screw diameter of between 4.0 and 8.5 millimeters. Preferably, the head 32 is semi-spherical in form other than at the flat surface surrounding the driver recess 32 and the portions of the head 30 which interface with the elongate body of the screw 20. A diameter of the screw head 30 is preferably similar to, but slightly longer than, a major diameter of the threads 34 on the screw 20. With such a small diameter, the head 30 is still as strong as other portions of the screw 20 and yet has a minimal diameter for a low profile form to accommodate varying anatomical and clinical situations.

Figure 3:
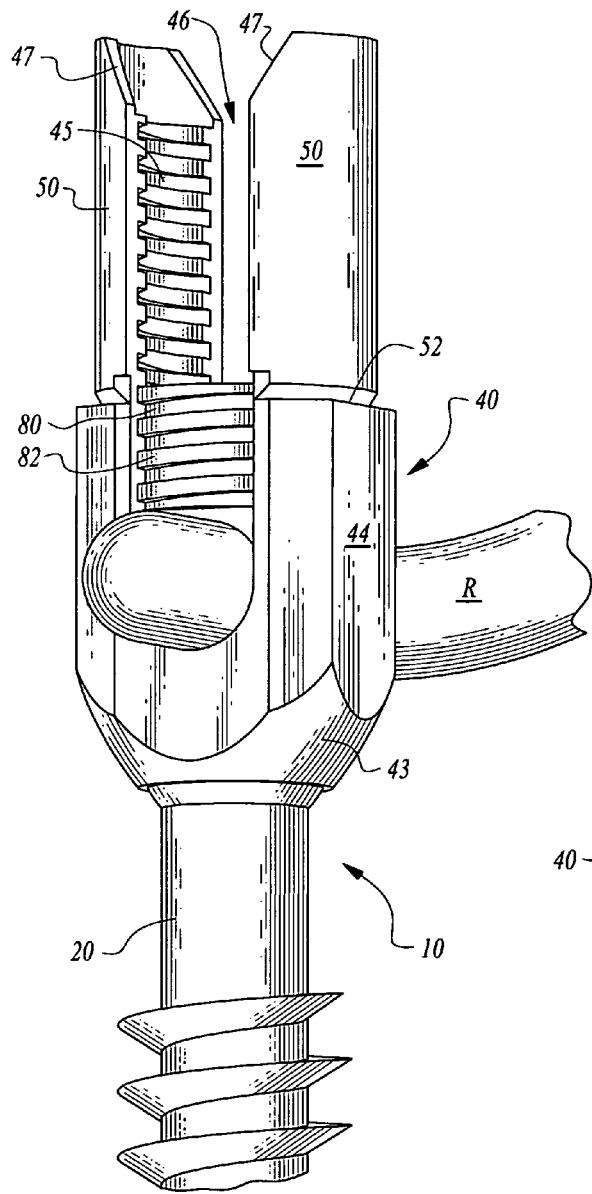
FIG. 3 is a detail of a portion of that which is shown in FIG. 1 showing details of the tulip head and spine rod portion of the pedicle screw.
Figure 4:
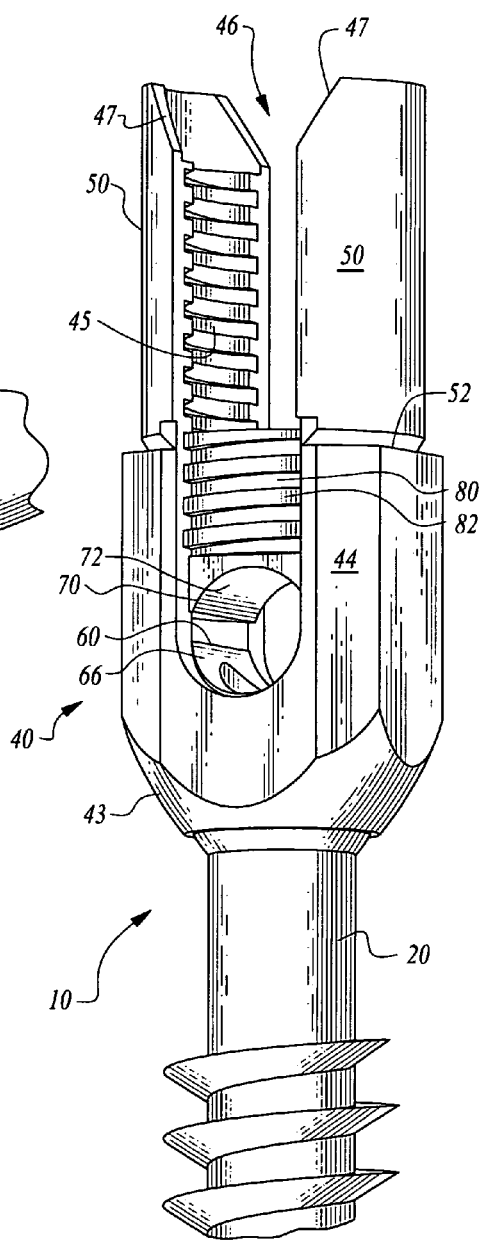
FIG. 4 is a perspective view similar to that which is shown in FIG. 3 but with the spine rod removed.
Figure 7:
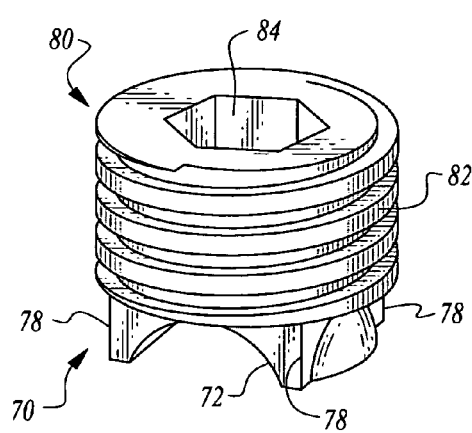
FIG. 7 is a perspective view of a locking nut and locking cap shown assembled together for securing the spine rod to the head of the pedicle screw.
Figure 8:
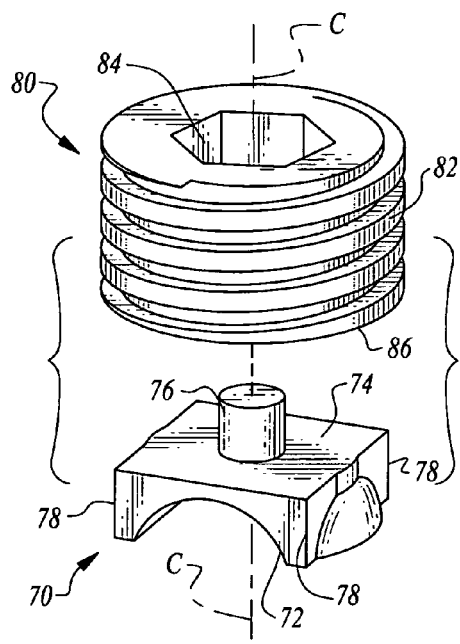
FIG. 8 is an exploded parts view of the locking nut and locking cap.

With particular reference to FIGS. 3, 4 and 6, details of the tulip head 40 are described, according to this most preferred embodiment. The tulip head 40 is a rigid mass typically formed of a material similar to that forming the screw 20, such as a titanium alloy that is biocompatible. The tulip head 40 has a generally cylindrical contour between a first end and a second end. These ends are open with one of the ends accommodating both the threads 34 of the screw 20 and the head 30 of the screw 20, and with the other of the ends only allowing the threads 34 to pass therethrough, but not allowing the head 30 to pass therethrough. This smaller end defines a collar 43 for the tulip head 40 which abuts against the head 30 and holds the head 30 within an interior of the tulip head 40.

The outer surface 44 of the tulip head 40 is preferably faceted to facilitate gripping and orienting of the tulip head 40 relative to the screw 20 either with fingers or with a rotating tool. Inner threads 45 are aligned with the centerline C of the tulip head 40. A slot 46 is oriented in a plane coextensive with this centerline C. The slot 46 stops short of the collar 43 but intersects through the end of the tulip head 40 opposite the collar 43. Preferably this end opposite the collar 42 is beveled with bevels 47 to more easily allow a spine rod R to be dropped into the slot 46 in the tulip head 40. The slot 46 is sized to receive the spine rod R therein, preferably with a width similar to a diameter of the spine rod R.

Portions of the tulip head 40 most distant from the collar 43 define break off tabs 50 above a notch 52 approximately midway between the ends of the tulip head 40. This notch 52 is sufficiently deep to allow the break off tabs 50 to be readily broken off of other portions of the tulip head 40. In some instances, it is desirable to have the break off tabs 50 initially attached to get the spine rod R into the slot 46 but still distant from an end of the slot 46 adjacent the collar 43. The locking nut 80 can then be advanced to cause the spine rod R to be drawn down into the slot 46 as far as possible. After the spine rod R has been tightened to the screw 20 through the tulip head 40, the break off tabs 50 are no longer required and can be bent at the notch 52 until they break off. The remaining tulip head 50 then has a lower profile at the implantation site. In other instances, where the break off tabs 50 are not required initially, the break off tabs 50 can be removed before the surgical procedure.

The inner surface of the tulip head 50 preferably includes a groove 54 (FIG. 6) extending between the ends and generally parallel with the centerline of the tulip head 40. This groove 54 thus intersects the inner threads 45. This groove 54 is configured to accommodate a key 68 (FIG. 2) in the saddle 60 or a tab 171 in an alternative locking cap 170 (FIGS. 9 and 10) as described in detail below.

With particular reference to FIGS. 2, 5 and 6, details of the saddle 60 are described, according to this most preferred embodiment. The saddle 60 is a rigid structure configured to reside within the tulip head 40 adjacent the collar 43 and between the spine rod R and the collar 43, and also abutting the head 30 of the screw 20. This saddle 60 preferably has a hollow core in which the head 30 can partially reside. A beveled lower lip 63 surrounds lateral edges of the head 30. Preferably, these beveled surfaces define the lower lip 63 and are beveled with a spherical contour having a radius of curvature matching a radius of curvature of the head 30 so that surface contact is provided between the beveled lower lip 63 of the saddle 60 and the head 30 of the screw 20.

The saddle 60 includes an outer wall 64 which is preferably cylindrical and resides inboard of the inner threads 45. A portion of the saddle 60 opposite the beveled lower lip 63 preferably includes a semi-cylindrical slot 66 therein having a curvature similar to a curvature of the spine rod R. Thus, this semi-cylindrical slot 66 provides a contact surface for engagement between the saddle 60 and the spine rod R. The saddle 60 thus maximizes surface contact between the head 30 of the screw 20 element and the spine rod R. By maximizing such surface contact, forces are best transferred between the spine rod R and the screw 20 element and minimizing potential for failure of the assembly 10 and rod R.

The saddle 60 can optionally include a key 68 extending from the outer wall 64. This key 68 is sized to reside within the groove 54 (FIG. 6) and the inner surface of the tulip head 40. Such a key 68 keeps the semi-cylindrical slot 66 of the saddle 60 aligned with the slot 46 in the tulip head 40. The key can sized slightly smaller than the groove 54 to accommodate some modification of position of the saddle 60 until tightened against the rod R and the tulip head 40.

With particular reference to FIGS. 5-8, details of the locking cap 70 and locking nut 80 are described, according to this most preferred embodiment. While the locking nut 80 can in one optional configuration bear directly upon the spine rod R and press the spine rod R against the head 30, either directly or through the saddle 60, most preferably the locking cap 70 is provided for bearing against portions of the spine rod R opposite the head 30. The locking cap 70 is a rigid structure which resides within the hollow interior of the tulip head 40. This locking cap 70 preferably is not threaded but has a top wall 74 which abuts the locking nut 80 which is threaded. The locking cap 70 includes a semi-cylindrical slot 72 on a side of the locking cap 70 opposite the top wall 74. This semi-cylindrical slot 72 has a cylindrical contour matching a contour of the spine rod R to provide surface contact against the spine rod R. As the locking nut 80 is tightened, the locking cap 70 is brought into tighter and tighter contact against the spine rod R through the semi-cylindrical slot 72.

Preferably, the locking cap 70 includes a post 76 extending from the top wall 74 and along the centerline C. This post 76 extends up into a hole 88 (FIG. 6) in the locking nut 80 to help to keep the locking cap 70 aligned with the locking nut 80. The locking nut 80 has outer threads 82 on a lateral surface which engage with the inner threads 45 of the tulip head 40. These outer threads 42 are preferably squared off in cross-sectional contour to facilitate easy start threading and to minimize potential for cross-threading. The pitch is sufficiently shallow to resist the locking cap 70 backing out after being tightened into the tulip head 40. The locking nut 80 includes a faceted recess 84 on a surface thereof most distant from the collar 43 of the tulip head 40. This faceted recess 84 can receive a torque applying tool, such as an allen wrench when the faceted recess 84 is a six sided hexagon. Other shaped recesses and tools could similarly work together to allow the locking nut 80 to be tightened by a tool interfacing within the faceted recess 84.

The lower surface 86 opposite the faceted recess 84 bears against the locking cap 70 to press the locking cap 70 against the spine rod R. The hole 88 preferably extends up into the lower surface 86 along the centerline C. This hole 88 accommodates the post 76 of the locking cap 70. The hole 88 can be sized just large enough to allow the post 86 to fit therein, or can be larger to allow some misalignment of the post 76 relative to the hole 88, at least initially before fully tightening the locking nut 80 against the locking cap 70.

The locking cap 70 preferably has a square perimeter contour featuring corners 78. These corners 78 can reside within four grooves within the inner surface of the tulip head 40 to keep the locking cap 70 aligned so that the semi-cylindrical slot 72 remains aligned with the slot 46 and the tulip head 40. Alternatively, rather than having the corners 78 or in addition to the corners 78, a tab can extend laterally from the locking cap 70 which can reside within the groove 54 in the tulip head 40 to keep the locking cap 70 properly aligned.

Figure 9:
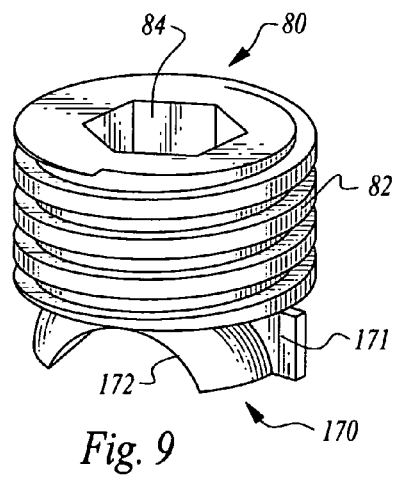
FIG. 9 is a perspective view of an alternative locking nut and locking cap shown adjacent each other.
Figure 10:
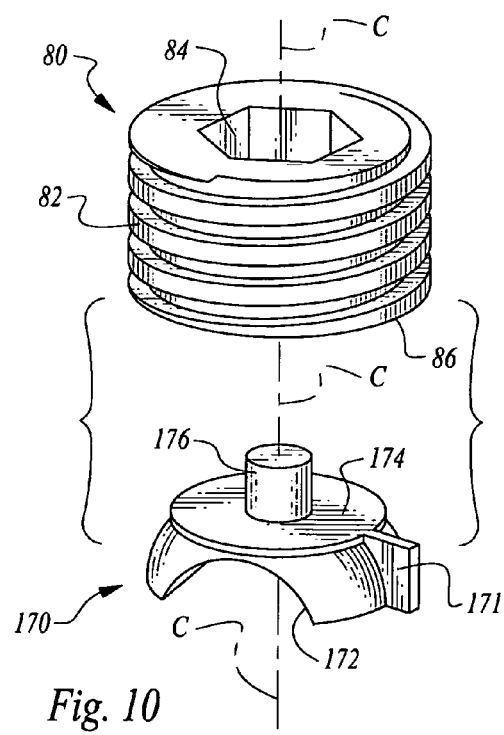
FIG. 10 is a perspective view of the locking nut and locking cap of this alternative embodiment of FIG. 9 exploded apart from each other.

In an alternative embodiment, an alternative locking cap 170 is provided adjacent the locking nut 80 (FIGS. 9 and 10). With the alternative locking cap 170 a tab 171 is provided which acts within the groove 54 to keep the alternative locking cap 170 aligned with the tulip head 40. This alternative locking cap 170 includes a semi-cylindrical slot 172 akin to that in the locking cap 70 of the embodiment of FIGS. 7 and 8. The alternative locking cap 170 has a more spherical contour but still includes a top wall 174 which is substantially flat for bearing against the lower surface 86 of the locking nut 80. A post 176 extends up from the top wall 174 and is sized to fit within the hole 88 of the locking nut 80.

In use and operation, and with particular reference to FIGS. 2, 3 and 5, details of the operation of the pedicle screw assembly 10 are described, according to this most preferred embodiment. Initially, the screw 20 element is placed through the tulip head 40 so that the tulip head 40 passes first over the tip 26 and then the screw 20 is advanced along the centerline C until the tulip head 40 has the collar 43 thereof abutting against the head 30 of the screw 20.

A guide wire can be utilized to pass into the pedicle of a vertebra and defining a line along which the screw 20 is to be attached. The screw 20 is then advanced along the guide wire passing through the central bore 28. A torque applying tool, which can also have a central bore for accommodating the guide wire, can be rotated to apply torque to the screw 20 and cause the screw 20 to bore into the pedicle of the vertebra. The screw 20 is advanced as far as desired by the medical professional. Once fully advanced, typically the guide wire would be removed. Next, the saddle 60 would typically be dropped into the interior of the tulip head 40.

The locking cap 70 and locking nut 80 can also be dropped into the interior of the tulip head 40 and the locking nut 80 at least initially advanced somewhat along the inner threads 45 of the tulip head 40. Once so positioned, the locking nut 80 keeps the locking cap 70 and saddle 60 captured within the tulip head 40 and reduces potential for loss of the separate structures.

In one embodiment the collar 43 of the tulip head 40 can be sized smaller than the head 30 of the screw 20, but sufficiently close in size that the collar 43 of the tulip head 40 can be snapped over the head 30, especially by utilizing a tool which can press the tulip head 40 down onto the screw 20. In such an embodiment the saddle 60, locking cap 70 and lock nut 80 can be preinstalled within the tulip head 40. With the saddle 60, locking cap 70 and lock nut 80 less than fully tightened, the spine rod R can be passed laterally through the slot 46 in the tulip head 40 and between the locking cap 70 and saddle 60. The lock nut 80 can then be further tightened until the locking cap 70 and saddle 60 are pressing against the spine rod R and are trapped at a lower end of the slot 46 and with at least the saddle 60 bearing on the head 30 of the screw 20, and potentially also portions of the spine rod R also directly bearing against the head 30 of the screw 20. The break off tabs 50 can be broken off either after tightening the lock nut 80 or before utilization of the tulip head 40.

Typically, a single spine rod R extends between at least two similar pedicle screws 20 extending into pedicles of separate vertebrae within the spine. Often two such spine rods are provided parallel to each other and spaced on lateral posterior sides of the spine. If desired, crosslinks can be provided joining the two spine rods together.

This disclosure is provided to reveal a preferred embodiment of the invention and a best mode for practicing the invention. Having thus described the invention in this way, it should be apparent that various different modifications can be made to the preferred embodiment without departing from the scope and spirit of this invention disclosure. When structures are identified as a means to perform a function, the identification is intended to include all structures which can perform the function specified. When structures of this invention are identified as being coupled together, such language should be interpreted broadly to include the structures being coupled directly together or coupled together through intervening structures. Such coupling could be permanent or temporary and either in a rigid fashion or in a fashion which allows pivoting, sliding or other relative motion while still providing some form of attachment, unless specifically restricted.

What is claimed is:

1. A pedicle screw, comprising in combination:
    a tip opposite a head, with a plurality of bone-engaging threads extending along a portion of the screw between said tip and said head;
    a tulip head having a rigid generally cylindrical hollow form with open ends, said tulip head including a slot formed along a centerline of a cylindrical contour of said tulip head, said tulip head including threads on an interior surface thereof, said open end of said tulip head at a first end sized large enough to allow both said threaded shaft and said head to pass therethrough and with a second end opposite said first end open and sized to allow said tip and said threads of the screw to pass therethrough, but to not allow said head of the screw to pass therethrough;
    a saddle adapted to reside within said interior of said tulip head, said saddle adapted to abut said head of the screw;
    a locking nut adapted to thread within said interior of said tulip head and apply a compression force against said spine rod toward said saddle, at least indirectly;
    wherein a locking cap is interposed between said nut and the rod, said locking cap including a semi-cylindrical slot on a side of said cap opposite said nut, said locking cap having a semi-spherical outer contour surrounding a substantially flat top wall; and
    said locking cap having a tab extending laterally therefrom and slidingly fit within a groove extending axially within said interior surface of said tulip head.

2. The pedicle screw of claim 1 wherein said saddle is sized to fit within said hollow interior of said tulip head, said saddle adapted to abut said head of the screw, said saddle having a semi-cylindrical surface on a side of said saddle most distant from said head of the screw, said semi-cylindrical surface adapted to abut the spine rod.

3. The pedicle screw of claim 2 wherein said saddle includes a beveled lower surface on a side of said saddle opposite said semi-cylindrical surface of said saddle, said beveled surface adapted to abut portions of said head of the pedicle screw.

4. The pedicle screw of claim 3 wherein said head of the screw is semi-spherical, and wherein said beveled lip of said saddle has a semi-spherical contour with a diameter of said semi-spherical contour of said beveled lip of said saddle matching a diameter of said semi-spherical contour of said head of the pedicle screw.

5. The pedicle screw of claim 1 wherein said locking cap includes a post extending from a surface of said locking cap opposite said semi-cylindrical surface; and
    said locking nut includes a hole extending into a surface of said locking nut abutting said locking cap, said hole sized to receive said post of said locking cap therein.

6. A pedicle screw and spine rod for spine immobilization, comprising in combination:
    a tip opposite a head, with a plurality of bone-engaging threads extending along a portion thereof between said tip and said head;
    said head having at least a portion of side walls thereof being semi-spherical;
    a tulip head having a rigid generally cylindrical hollow form with open ends, said tulip head including a slot formed along a centerline of a cylindrical contour of said tulip head, said tulip head including threads on an interior surface thereof, said open end of said tulip head at a first end sized large enough to allow both said threaded shaft and said head to pass therethrough and with a second end opposite said first end open and sized to allow said tip and said threads of the screw to pass therethrough, but to not allow said head of the screw to pass therethrough;
    an elongate substantially rigid spine rod, said spine rod having a circular cross-section, said spine rod secured within said slot of said tulip head between said head of the screw and said locking nut;
    a locking nut adapted to thread within said interior of said tulip head and apply a compression force against said spine rod toward said head, at least indirectly;
    wherein a locking cap is interposed between said nut and the rod, said locking cap including a semi-cylindrical slot on a side of said cap opposite said nut, said locking cap having a semi-spherical outer contour, surrounding a substantially flat top wall;
    wherein a saddle is sized to fit within said hollow interior of said tulip head, said saddle adapted to abut said head of the screw, said saddle having a semi-cylindrical surface on a side of said saddle most distant from said head of the screw, said semi-cylindrical surface adapted to abut the spine rod; and
    said locking cap having a tab extending laterally therefrom and slidingly fit within a groove extending axially within said interior surface of said tulip head.

7. The pedicle screw and spine rod combination of claim 6 wherein said spine rod has a curving contour curving in a direction relative to the spine to increase lordosis in the spine.

* * * * *